United States Patent [19]

Gajda

[11] Patent Number: 5,744,686
[45] Date of Patent: Apr. 28, 1998

[54] PROCESS FOR THE REMOVAL OF NITROGEN COMPOUNDS FROM AN AROMATIC HYDROCARBON STREAM

[75] Inventor: Gregory J. Gajda, Mt. Prospect, Ill.

[73] Assignee: UOP, Des Plaines, Ill.

[21] Appl. No.: 530,979

[22] Filed: Sep. 20, 1995

[51] Int. Cl.⁶ .............................. C07C 7/12; C07C 7/00; C25D 3/34
[52] U.S. Cl. .................. 585/823; 585/804; 585/805; 585/448; 585/518; 585/717; 208/254 R; 208/299; 208/300; 423/239.2
[58] Field of Search .................. 585/823, 804, 585/805, 717, 448, 518; 208/254 R, 299, 300; 423/239.2

[56] References Cited

U.S. PATENT DOCUMENTS

| | | | |
|---|---|---|---|
| 4,061,724 | 12/1977 | Grose et al. | 423/335 |
| 4,073,865 | 2/1978 | Flanigen et al. | 423/339 |
| 4,107,224 | 8/1978 | Dwyer | 260/671 |
| 4,185,040 | 1/1980 | Ward et al. | 585/467 |
| 4,774,377 | 9/1988 | Barger et al. | 585/323 |
| 4,891,458 | 1/1990 | Innes et al. | 585/323 |
| 5,030,786 | 7/1991 | Shamshoum et al. | 585/467 |
| 5,220,102 | 6/1993 | Funk et al. | 585/829 |
| 5,271,835 | 12/1993 | Gorawara et al. | 208/228 |

*Primary Examiner*—Glenn Caldarola
*Assistant Examiner*—In Suk Bullock
*Attorney, Agent, or Firm*—Thomas K. McBride; John G. Tolomei; Richard P. Silverman

[57] ABSTRACT

This invention relates to a process for the removal of nitrogen compounds from an aromatic hydrocarbon stream comprising the nitrogen compounds by contacting the hydrocarbon stream with a selective adsorbent having an average pore size less than about 5.5 Angstroms. The selective adsorbent is a molecular sieve selected from the group consisting of pore closed zeolite 4A, zeolite 4A, zeolite 5A, silicalite, F-silicalite, ZSM-5 and mixtures thereof. In one embodiment, the present invention comprises a combination of a fractionation zone and an adsorption zone wherein the feedstream is passed to the fractionation zone to provide a dry bottoms product stream essentially free of the nitrogen compounds and an overhead stream. The overhead stream is condensed to provide an aqueous stream and a hydrocarbon stream. The hydrocarbon stream is passed to an adsorption zone and a treated effluent recovered therefrom is returned to the fractionation zone. The invention provides significant cost advantages when the feedstream is subject to slugs or surges in levels of nitrogen compounds which can be detrimental to downstream catalyst as found in aromatic conversion reactions.

25 Claims, 1 Drawing Sheet

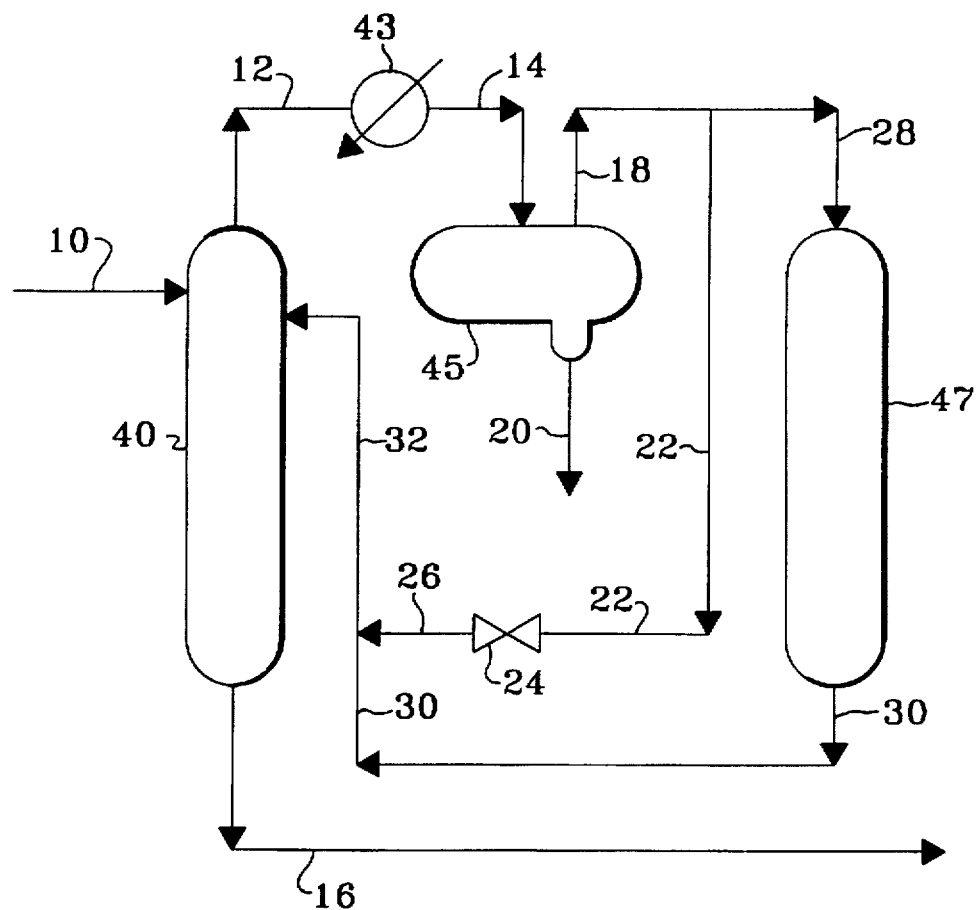

5,744,686

1

PROCESS FOR THE REMOVAL OF NITROGEN COMPOUNDS FROM AN AROMATIC HYDROCARBON STREAM

FIELD OF THE INVENTION

This invention relates to a process for removing nitrogen compounds from a fluid stream. More particularly, this invention relates to the use of a selective adsorption process containing an adsorbent selective for nitrogen compounds to remove nitrogen compounds from a fluid stream to protect an aromatic conversion catalyst.

BACKGROUND OF THE INVENTION

The use of molecular sieves as catalysts in aromatic conversion processes are well known in the chemical processing and refining industry. Aromatic conversion reactions of considerable commercial importance include the alkylation of aromatic compounds such as in the production of ethyltoluene, xylene, ethylbenzene, cumene, or higher alkyl aromatics and in disproportionation reactions such as toluene disproportionation, xylene isomerization, or the transalkylation of polyalkylbenzenes to monoalkylbenzenes. Often the feedstock to such an aromatic conversion process will include an aromatic component, such as benzene, and a $C_2$ to $C_4$ olefin alkylating agent or a polyalkyl aromatic hydrocarbon transalkylating agent.

The catalysts for such alkylation or transalkylation reactions generally comprise zeolite molecular sieves. Innes et al., U.S. Pat. No. 4,891,458 discloses the presence of a catalyst comprising zeolite beta. Shamshoum et al., U.S. Pat. No. 5,030,786 discloses an aromatic conversion process employing zeolite Y, zeolite omega and zeolite beta molecular sieve catalyst. Ward et al., U.S. Pat. No. 4,185,040 discloses the ) alkylation of benzene to produce ethylbenzene or cumene employing zeolites such as molecular sieves of the X, Y, L, B, ZSM-5 and Omega crystal types. Barger et al., U.S. Pat. No. 4,774,377, discloses an aromatic conversion process involving alkylation over a catalyst comprising a solid phosphoric acid component followed by transalkylation using aluminosilicate molecular sieve transalkylation catalysts including X, Y, ultrastable Y, L, Omega, and mordenite zeolites. The above U.S. Patents are hereby incorporated by reference.

Molecular sieve catalysts employed in alkylation reactions in the vapor or the liquid phase may be sensitive to impurities such as water at various levels or sulfur compounds in the feedstock. Dwyer, U.S. Pat. No. 4,107,224, discloses that water and hydrogen sulfide in vapor phase reactions may be tolerable if more rapid aging of the catalyst is acceptable. Shamshoum et al, ibid, disclose the dehydration of the feedstock to a water content of no more than 100 ppm, and preferably 50 ppm or less when the reaction zone is operated to maintain the reactor contents in the liquid phase.

The drying of hydrocarbon liquids is generally accomplished by adsorption of the water by passing the liquid over a suitable adsorbent such as activated alumina, silica gel, or fuller's earth. In the drying of liquids, the wet liquid is passed through one chamber while another is being dried. The feed is usually passed upwardly through the chamber so that slugs of water laden liquid may settle before it contacts the adsorbent. The spent adsorbent is regenerated by draining or steaming the liquid from the adsorbent and passing hot gas or superheated steam through the adsorbent at elevated temperatures.

Fractionation is widely used for drying liquids that are substantially immiscible with water such as propane or hydrocarbon oils. The low boiling product of such a system is a constant boiling mixture of water and the hydrocarbon in proportion to their relative vapor pressure. Upon condensation the constant boiling mixture separates into a hydrocarbon layer and a water layer.

Funk et al., U.S. Pat. No. 5,220,102 disclose a chromatographic process for separating linear olefins from mixtures of branched olefins with a high silica zeolite molecular sieve, e.g., silicalites, ZSM-5, etc., having low acid catalyst reactivity which selectively adsorbs the normal olefins and uses ketones as desorbents.

Flanigen et al., U.S. Pat. No. 4,073,865 disclose a silica polymorph and a process for preparing the silica polymorph having a fluoride content and a low alumina content. The presence of the fluoride anion and the low alumina content in such fluoride-silicalites (F-silicalites) provide a crystalline silica composition which is extremely hydrophobic and is useful for separations requiring minimum water adsorption in the adsorption of less polar materials or where the presence of surface hydroxyl groups or adsorbed water would react with or catalyze reactions of the feed and/or product streams. The U.S. Pat. Nos. 4,073,865 and 5,220,102 patents are hereby incorporated by reference.

Gorawara et al., U.S. Pat. No. 5,271,835, discloses the presence of polar impurities in the $C_3$–$C_5$ product fraction from a fluid catalytic cracking unit. The impurities were found to include nitrogen compounds such as acetonitrile.

When impurities are present in the feedstock to an aromatic conversion reactor, particularly basic impurities such as nitrogen compounds, the catalyst performance and the catalyst life may be adversely affected. As more active zeolite catalysts are employed in aromatic conversion reactions, the degradation of catalyst life by nitrogen impurities in the feedstock must be more carefully controlled. Processes are sought to reduce the impact of nitrogen impurities on the catalyst in the reaction zone.

SUMMARY OF THE INVENTION

The present invention relates to the drying of a feedstream to a catalytic process containing a catalyst wherein the feedstream also contains a trace impurity such as a nitrogen compound which is detrimental to the catalyst. By the present invention, a process is provided for the removal of nitrogen compounds from an aromatic hydrocarbon stream comprising the nitrogen compounds and mixtures thereof with water. The process comprises passing the aromatic hydrocarbon stream to an adsorption zone containing an adsorbent selective for the adsorption of said nitrogen compounds. The adsorbent comprises a non-acidic molecular sieve having a silica to alumina ratio in excess of about 100 and having an average pore size less than about 5.5 Angstroms. A treated effluent being essentially free of the nitrogen compounds is withdrawn from the adsorption zone. The advantage of the present invention is that the adsorbent can remove the nitrogen compound which is a polar compound from the aromatic hydrocarbon stream in the presence of water.

The problem of applying traditional drying methods to removing both the water and the trace nitrogen compound results in a very expensive or oversized dryer, particularly when the nitrogen compound appears as slugs or concentration peaks in the feedstream. In one embodiment, the present invention integrates the adsorption of the nitrogen compound with a fractionation scheme which results in a simplified process wherein the separation of the nitrogen compound is accomplished by indirect treatment of the product stream, and the product stream is produced essentially free of the nitrogen compound. The advantage of the invention is a less costly process which provides a high recovery of the treated product. The synergy provided by the combination of fractionation and adsorption by the process of the present invention provides a highly efficient, low cost process which is superior to either fractionation or adsorption alone.

In one embodiment a process is provided for the alkylation of a benzene stream with a light olefin having 2–3 carbon atoms per molecule to form an alkylate product. The benzene stream comprises a nitrogen compound as an impurity. The process comprises passing the benzene stream to a guard bed containing a molecular sieve which is selective for the adsorption of the nitrogen compound. The molecular sieve has an average pore size less than about 5.5 Angstroms. A treated feedstream essentially free of the nitrogen compound is produced. The treated feedstream is alkylated with the light olefin over an acid catalyst to produce an alkylate product. The adsorbent selective for the adsorption of the nitrogen compound is selected from the group consisting of silicalite and F-silicalite.

In another embodiment, a process is provided for the removal of a nitrogen compound from a mixture of the nitrogen compound, water, and an aromatic hydrocarbon component. The process comprises passing the mixture to a fractionation zone to provide an overhead stream comprising the nitrogen compound, water, and the aromatic hydrocarbon component and a bottoms product stream being essentially free of the nitrogen compound. The overhead stream is cooled and condensed to produce a hydrocarbon phase stream comprising the nitrogen compound and water and an aqueous phase stream comprising the nitrogen compound. The aqueous phase stream is withdrawn. The hydrocarbon phase stream is passed to an adsorption zone containing an adsorbent selective for the adsorption of the nitrogen compound. A treated effluent stream essentially free of the nitrogen compound is withdrawn from the adsorption zone and returned to the fractionation zone. The passing of the hydrocarbon phase stream to the adsorption zone is terminated, and at least a portion of the hydrocarbon phase stream is returned to the fractionation zone. The adsorption zone is regenerated to provide a regenerated adsorption zone. The returning of the hydrocarbon phase stream to the fractionation zone is terminated and the passing of the hydrocarbon phase stream to the regenerated adsorption zone is resumed to provide a continuous process.

BRIEF DESCRIPTION OF THE DRAWING

The FIGURE is a schematic flow diagram of one embodiment of the process of the present invention wherein an adsorbent bed is integrated with a fractionation zone.

DETAILED DESCRIPTION OF THE INVENTION

The hydrocarbon feedstream of this invention is generally a liquid and comprises from about 0.001 to about 20 mol % nitrogen compounds. The feedstream may comprise water up to saturation conditions. The aromatic hydrocarbon feedstream is selected from the group consisting of benzene, toluene, xylenes, and mixtures thereof. When the hydrocarbon feedstream is an aromatic hydrocarbon for an alkylation reaction, the hydrocarbon feedstream comprises from about 5 to 99.9 mol-% benzene.

The feedstream is charged to an adsorption zone to adsorb nitrogen compounds such as acetonitrile, propionitrile, acrylonitrile, and mixtures thereof, and provide a treated adsorption effluent, depleted in nitrogen compounds. In the adsorption zone, the most readily adsorbable component, nitrogen compounds, is adsorbed and the less readily adsorbable components, the aromatic hydrocarbons, are passed through the adsorption zone and are withdrawn in an adsorption effluent. The adsorption zone pressure is from about 100 to about 3450 kPa (about 15 to about 500 psia). The adsorption zone temperature is any temperature effective to adsorb the more readily adsorbable components in the feedstream, and preferably from about −18° C. to about 205° C. (about 0° to about 400° F.). It is to be understood that the adsorption zone of the present invention contains one or more fixed beds containing an adsorbent suitable for adsorbing the particular components to be adsorbed therein. As the capacity of the adsorption bed for the most readily adsorbable component is reached; that is, preferably before a substantial portion of the leading adsorption front has passed through the first adsorption bed, the feedstream is directed to another bed in the adsorption zone or the process is stopped and the adsorption bed is regenerated with a hot natural gas stream by a carbon burn or other conventional method. The term "enriched" is intended to be with reference to the feedstream composition unless otherwise noted.

The term "essentially pure"—as used herein and referring to the product stream—means that the product stream preferably comprises greater than about 97 wt-% of the aromatic hydrocarbon, and most preferably the bottoms product comprises greater than 99 wt-% of the aromatic hydrocarbon. The term "essentially free"—as used herein and referring to the treated effluent or product stream—means that the treated effluent preferably comprises less than about 1 ppm-wt of the nitrogen compound, and more preferably the treated effluent comprises less than about 0.1 ppm-wt of the nitrogen component. The aqueous stream withdrawn from the process of the present invention comprises less than about 0.3 wt-% of the aromatic hydrocarbon. Preferably, the aqueous stream withdrawn from the process comprises less than about 1 wt % of the feedstream and most preferably, the aqueous stream comprises less than about 0.1 wt-% of the feedstream.

Suitable adsorbents known in the art and commercially available include crystalline molecular sieves, activated carbons, activated clays, silica gels, activated aluminas and the like. Such adsorbent material or mixtures thereof will be understood to be suitable if the adsorbent material is capable of selectively adsorbing impurities such as nitrogen compounds and water from a fluid stream. The molecular sieves include, for example, the various forms of silicoaluminophosphates, and aluminophosphates disclosed in U.S. Pat. Nos. 4,440,871; 4,310,440 and 4,567,029, hereby incorporated by reference as well as zeolitic molecular sieves.

As used here, the term "molecular sieve" is defined as a class of adsorptive desiccants which are highly crystalline in nature, distinct from amorphous materials such as gamma-alumina. Preferred types of molecular sieves within this class of crystalline adsorbents are aluminosilicate materials commonly known as zeolites. The term "zeolite" in general refers to a group of naturally occurring and synthetic hydrated metal aluminosilicates, many of which are crystalline in structure. There are, however, significant differences between the various synthetic and natural materials in chemical composition, crystal structure and physical properties such as x-ray powder diffraction patterns. The zeolites occur as agglomerates of fine crystals or are synthesized as fine powders and are preferably tableted or pelletized for large-scale adsorption uses. Pelletizing methods are known which are very satisfactory because the sorptive character of the zeolite, both with regard to selectivity and capacity, remains essentially unchanged.

The pore size of the zeolitic molecular sieves may be varied by employing different metal cations. For example, sodium zeolite A has an apparent pore size of about 4 Å units, whereas calcium zeolite A has an apparent pore size of about 5 Å units. The term "apparent pore size" as used herein may be defined as the maximum critical dimension of the molecular sieve in question under normal conditions. The apparent pore size will usually be larger than the effective pore diameter, which may be defined as the free diameter of the appropriate silicate ring in the zeolite structure.

Zeolitic molecular sieves in the calcined form may be represented by the general formula;

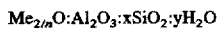

$Me_{2/n}O:Al_2O_3:xSiO_2:yH_2O$ where Me is a cation, x has a value from about 2 to infinity, n is the cation valence and y has a value of from about 2 to 10. Typical well-known zeolites which may be used include chabazite, also referred to as Zeolite D, clinoptilolite, erionite, faujasite, also referred to as Zeolite X and Zeolite Y, ferrierite, mordenite, Zeolite A, and Zeolite P. Other zeolites suitable for use according to the present invention are those having a high silica content, i.e., those having silica to alumina ratios greater than 10 and typically greater than 100. One such high silica zeolite is silicalite, as the term used herein includes both the silicapolymorph disclosed in U.S. Pat No. 4,061,724 and also the F-silicate disclosed in U.S. Pat. No. 4,073,865, hereby incorporated by reference. Detailed descriptions of some of the above-identified zeolites may be found in D. W. Breck, *Zeolite Molecular Sieves*, John Wiley and Sons, New York, 1974, hereby incorporated by reference.

The preferred adsorbents for this separation are the high silica zeolites having a silica:alumina mole ratio of at least about 300, including ZSM-5 and silicalite, and a pore size of about 5.5 Angstroms in diameter. Such zeolites and their preparations are well known, for example, from U.S. Pat. Nos. 4,309,281 to Dessau and 4,061,724 and 4,104,294 to Grose et al. A more detailed discussion of silicalite may be found in the article, "Silicalite, A New Hydrophobic Crystalline Silica Molecular Sieve;" NATURE, Vol. 271, Feb. 9, 1978, incorporated herein by reference. Also useful are fluoride silicalites, such as those described in U.S. Pat. No. 4,073,865 to Flanigen et al. The fluoride silicalites have a pore diameter of about 6 Angstroms. Fluoride silicalites are exceptionally inert and do not catalyze olefinic reactions. The silicalites used in the separation process of the invention have silica to alumina ratios $(SiO_2/Al_2O_3)$ of at least 100 and preferably in the range of 700 to 1000.

The adsorbents are preferably bonded with a binder material, such as silica, which is an amorphous material having channels and cavities enabling access by the components to be separated and by the desorbent to the adsorbent. The binder aids in forming or agglomerating the crystalline particles of the silicalite which otherwise would comprise a fine powder.

The silicalite molecular sieve may then be formed into particles such as extrudates, aggregates, tablets, macrospheres or granules having a desired particle range, preferably from about 16 to about 60 mesh (Standard U.S. Mesh) (1.9 mm to 230 μm).

Colloidal amorphous silica is an ideal binder for silicalite in that it exhibits essentially no reactivity with olefins in the feed. A silica marketed by DuPont Co. under the trademark Ludox and another marketed by Nalco Chemical Co. (1034) are preferred. The silicalite powder is dispersed in the colloidal amorphous silica which is then gelled and may be further treated in a manner so as to substantially eliminate hydroxyl groups, such as by thermal treatment in the presence of oxygen at a temperature from about 450° C. to about 850° C. for a minimum period from about 3 hours to about 48 hours. The silicalite should be present in the silica matrix in amounts ranging from about 75 wt % to about 98 wt % silicalite based on volatile-free composition.

The extruded bonded silicalite particles are thoroughly mixed with a solution of a soluble alkali metal compound such as a sodium bicarbonate, sodium phenoxide, sodium methoxide, sodium hyponitrite, sodium iodate, sodium tartrate, sodium thiosulfate, potassium hypochlorite, potassium carbonate, potassium nitride, potassium oxalate, potassium succinate, rubidium bicarbonate, rubidium dichlorobromide and rubidium sulfate. Finally, the mixture is dried and calcined at a temperature of at least 700° C., up to about 1000° C., preferably in the range 800° C. to 900° C. This adsorbent has been determined to be virtually non-reactive under conditions of the adsorption separation of the invention (i.e., no isomerization or formation of heavy products when olefinic feed is contacted with the adsorbent over night in a pressure vessel, such as a Parr bomb, at 175° C.).

The adsorbent may be employed in the form of a dense fixed bed which is alternately contacted with a feed mixture and a desorbent material in which case the process will be only semi-continuous. In an other embodiment a set of two or more static beds of adsorbent may be employed with appropriate valving so that a feed mixture can be passed through one or more adsorbent beds of a set while a desorbent material can be passed through one or more of the other beds in a set. The flow of a feed mixture and a desorbent material may be either up or down through an adsorbent in such beds. Any of the conventional apparatus employed in static bed fluid-solid contacting may be used.

In the selective alkylation of aromatics by olefins as catalyzed by an acid catalyst, the olefins may contain from 2 up to at least 20 carbon atoms, and may be branched or linear olefins, either terminal or internal olefins. Thus, the specific nature of the olefin is not particularly important. What the allations share in common is that the reactions are conducted under at least partially liquid phase conditions, a criterion readily achieved for the lower members by adjusting reaction pressures. Among the lower olefins, ethylene and propylene are the most important representatives. Among the remaining olefins, the class of detergent range olefins is of particular interest. This class consists of linear olefins containing from 6 up through about 20 carbon atoms which have either internal or terminal unsaturation. Linear olefins containing from 8 to 16 carbon atoms are particularly usefull as detergent range olefins, and those containing from 10 up to about 14 carbon atoms are especially preferred.

Benzene is by far the most important representative of the alkylatable aromatic compounds which may be used in the practice of the invention. More generally the aromatic compounds may be selected from the group consisting of benzene, naphthalene, anthracene, phenanthrene, and substituted derivatives thereof. The most important class of substituents found on the aromatic nucleus of alkylatable aromatic compounds are alkyl moieties containing from 1 up to about 20 carbon atoms. Another important substituent is the hydroxyl moiety as well as the alkoxy moiety whose alkyl group also contains from 1 up to 20 carbon atoms. Where the substituent is an alkyl or alkoxy group, a phenyl moiety also can be substituted on the paraffinic chain. Although unsubstituted and monosubstituted benzenes, naphthalenes, anthracenes, and phenanthrenes are most often used in the practice of this invention, polysubstituted aromatics also may be employed. Examples of suitable alkylatable aromatic compounds in addition to those cited above include biphenyl, toluene, xylene, ethylbenzene, propylbenzene, butylbenzene, pentylbenzene, hexylbenzene, heptylbenzene, octylbenzene, and so forth; phenol, cresol, anisole, ethoxy-, propoxy-, butoxy-, pentoxy-, hexoxybenzene, and so forth.

The particular conditions under which the alkylation reaction is conducted depends upon the aromatic compound and the olefin used. Since the reaction is conducted under at least partial liquid phase conditions, reaction pressure is adjusted to maintain the olefin at least partially in the liquid phase. For higher olefins the reaction may be conducted at autogenous pressure. As a practical matter the pressure normally is in the range between about 200 and about 1,000 psig (1379–6985 kPa) but usually is in a range between about 300–600 psig (2069–4137 kPa). But we emphasize again that pressure is not a critical variable and needs to be sufficient only to maintain at least partial liquid phase conditions. Representative alkylation temperatures include a range of between 200°–250° C. for alkylation of benzene with ethylene and temperatures of 90°–160° C. for the alkylation of benzene by propylene. The temperature range appropriate for alkylation of the alkylatable aromatic compounds of our invention with the olefins in the $C_2$–$C_2$ range is between about 60° and about 400° C., with the most usual temperature range being between about 90° and 250° C.

The ratio of alkylatable aromatic compound to olefin used in the process which is our invention will depend upon the degree of selective alkylation desired as well as the relative costs of the aromatic and olefinic components of the reaction mixture. For alkylation of benzene by propylene, benzene-to-olefin ratios may be as low as about 2 and as high as about 10, with a ratio of 2.5–8 being preferred. Where benzene is alkylated with ethylene a benzene-to-olefin ratio between about 1:1 and 8:1 is preferred. For detergent range olefins of $C_6$–$C_{20}$, a benzene-to-olefin ratio of between 5:1 up to as high as 30:1 is generally sufficient to ensure the desired alkylation selectivity, with a range between about 8:1 and about 20:1 even more highly desired.

In one embodiment, the present invention relates to a process for the drying and removal of a trace impurity such as a nitrogen compound from an aromatic hydrocarbon feedstream by adsorption and more particularly by the combination of a fractionation zone and an adsorption zone. According to this embodiment the aromatic hydrocarbon feedstream comprising the trace impurity and water is passed to the fractionation zone to provide an overhead stream, comprising water and the impurity, and a bottoms product stream comprising essentially no impurity. The overhead stream is cooled, condensed, and separated to provide a hydrocarbon phase stream and an aqueous stream. The aqueous stream is withdrawn and passed to conventional water treatment facilities. The hydrocarbon phase stream is passed to an adsorption zone in an adsorption step containing an adsorbent selective for the adsorption of the trace impurity to produce a treated hydrocarbon phase stream having a reduced amount of impurity relative to the feedstream, and the treated hydrocarbon phase stream is returned to the fractionation zone. When the concentration of impurity in the treated hydrocarbon phase stream reaches a level greater than about 0.1 wt-% impurity, the adsorption zone is isolated and the adsorbent is regenerated in the conventional manner. The preferred regeneration procedure comprises draining the adsorption zone and passing the contents to the fractionation zone; desorbing the adsorbed impurity with a desorbent such as steam, hot gas, or natural gas. Following desorption the adsorption zone is cooled to the adsorption temperature by introducing at least a portion of the bottoms product from the fractionation zone until the adsorption temperature is reached. The portion of the bottoms product withdrawn from the regenerated bed in this manner may be passed directly to an alkylation reactor for the alkylation of an aromatic feedstream comprising benzene. At the completion of the cooling step, the first adsorption bed is isolated to provide a regenerated adsorption zone filled with bottoms product. The first adsorption is returned to the adsorption mode by reintroducing the hydrocarbon phase stream and returning the portion of the bottoms product which is displaced from the regenerated adsorption zone to the fractionation zone without a separate drain step.

During the above regeneration steps, the hydrocarbon phase stream may be passed to another adsorption bed or alternatively returned to the fractionation zone as reflux. It is preferred that the feed to the fractionation zone be at a feedpoint in an upper portion of the fractionation zone and that the reflux stream be reintroduced to the fractionation zone at a point below the feed point to obtain good separation and maintain bottoms product quality. The withdrawing of the bottoms product from the fractionation zone is continued during the regeneration of the first adsorption zone. At this point in the process, the concentration of the impurity throughout the fractionation zone increases as the hydrocarbon comprising the impurity is reintroduced to the fractionation zone. Because the impurity is distilled overhead with the top product, the fractionation zone provides a buffer that prevents the impurity concentration from entering the bottom of the column for a time period. As the level of impurity builds in the fractionation zone, the concentration of the impurity in the bottoms product slowly increases in a dynamic fashion. The time constant of the fractionation zone or the time when concentration of the impurity in the bottoms product will reach 63% of the concentration of the impurity in the feedstream is preferably greater than about 2 times the regeneration time or the time required to regenerate the adsorption zone such that the concentration of the impurity in the bottoms product remains at or below a desirable level of impurity in a continuous process. More preferably the time constant of the fractionation zone is about 2 to about 10 times the regeneration time. A second adsorption bed may be employed in the adsorption zone to ensure that the concentration of impurity in the bottoms product does not exceed the desired level of impurity when a slug of impurity or concentration spike is introduced in the feedstream. When a second adsorption bed is employed, the first and second adsorption beds may be alternated in the conventional manner such that one bed is in the adsorption mode while the other bed is regenerated. In the event of a concentration spike in the feedstream, a portion of the hydrocarbon phase may by-pass the adsorption zone and be sent directly to the fractionation zone for a period of time while the first and second adsorption beds are regenerated.

DETAILED DESCRIPTION OF THE DRAWING

The further description of one embodiment of the process of this invention is presented with reference to the attached FIGURE. The FIGURE represents aspects of one embodiment of the invention and are not intended to be a limitation on the generally broad scope of the invention as set forth in the claims. Of necessity, some miscellaneous appurtenances—including valves, pumps, separators, heat exchangers, etc.—have been eliminated. Only those vessels and lines necessary for a clear and complete understanding of the process of the present invention are illustrated. In all cases, the process is a continuous process. The associated piping and manifolding for switching the adsorbent bed between adsorption and regeneration and the sequencing thereof are well known to those in the adsorption art.

Referring to the FIGURE, a benzene feedstream 10 is passed to a drying column 40 to remove water and nitrogen impurities from the benzene feedstream and to produce a treated benzene stream 16 comprising less than about 0.1 ppm-wt nitrogen impurities and less than about 10 ppm-wt water. Preferably the drying column will contain from 5–20 theoretical trays. The actual number of theoretical trays required for a specific case may be determined by conventional methods by one skilled in the art of drying hydrocarbon streams by distillation. The benzene feedstream 10 enters the drying column at a feed point. The benzene feedstream is water-saturated having about 300 to about 600 ppm-wt water and comprising about 1 to about 50 ppm-wt nitrogen compounds, such as acetonitrile and propionitrile. Preferably, the benzene feedstream comprises less than about 20 ppm-wt acetonitrile, and more preferably, the benzene feedstream comprises less than about 10 ppm-wt acetonitrile.

An overhead stream 12 comprising water, benzene and nitrogen compounds is removed from the drying column 40 and is passed to a condenser 43 wherein the overhead stream is at least partially condensed to provide a cooled overhead stream 14. The cooled overhead stream 14 is passed to an accumulator 45 to permit an aqueous phase and a hydrocarbon phase to form. The aqueous phase containing primarily water and a small amount of hydrocarbon and acetonitrile is removed in line 20, and the hydrocarbon phase stream comprising benzene and acetonitrile is passed via lines 18 and 28 to an adsorbent bed 47. The small amount of hydrocarbon and acetonitrile removed in line 20 is preferably less than about 0.5 wt-% of the benzene feedstream and more preferably the amount of hydrocarbon removed in line 20 with the aqueous phase is less than about 0.1 wt-% of the benzene feedstream. The adsorbent bed 47 contains an adsorbent selective for the adsorption of nitrogen compounds such as acetonitrile in the presence of benzene. During an adsorption mode of operation, adsorbent effluent comprising less than about 0.1 ppm-wt acetonitrile, i.e., essentially free of nitrogen compounds, is removed from the adsorbent bed 47 in line 30 and line 32. At least a portion of the adsorbent effluent stream is returned to the drying column at a point near the top of the drying column via line 32 as a reflux stream. The adsorption mode operation is terminated at a point in the adsorption cycle prior to the breakthrough of acetonitrile in the adsorption effluent 30. At this point, the hydrocarbon phase stream 18 is by-passed around the adsorbent bed 47 via lines 18 and 22, valve 24 and lines 26 and 32 to the drying column 40 at a point near the top of the drying column and below the feed point. The adsorbent bed 47 is regenerated in a regeneration mode. The adsorbent bed 47 may be regenerated in the conventional manner first draining the bed and returning the liquid to the drying column 40, followed by a desorption step wherein a hot desorbent such as fuel gas or nitrogen is introduced at a desorption temperature of about 150° C. to about 350° C. to desorb the acetonitrile from the selective adsorbent and provide a regenerated bed. At the completion of the desorption step, the regenerated bed is cooled to an adsorption temperature of about 20° C. to about 60° C. prior to introducing the hydrocarbon phase 28 to the adsorbent bed 47 to resume the adsorption of the impurity. In a preferred method, the regenerated bed is cooled by passing a portion of the bottoms product 16 to the regenerated bed. When the regenerated bed reaches the adsorption temperature, the passing of the portion of the bottoms product to the regenerated bed is terminated, retaining a portion of the bottoms product in the bed.

When using the adsorbent bed in the adsorbent mode, at least a portion of the reflux stream 32 is returned to the drying column at a point below the point where the benzene feedstream 10 enters the column. The return of at least a portion of the reflux stream at a point below where the benzene feedstream enters the column was found to substantially improve the efficiency of the removal of water and acetonitrile from the benzene feedstream.

When concentration of the nitrogen compounds such as acetonitrile is relatively constant, the present invention may be practiced with a drying column and a single adsorption bed. During the regeneration of the adsorption bed, the drying column continues to produce a dry benzene product, essentially free of acetonitrile as described hereinabove. In an alternate embodiment, when the concentration of the nitrogen compounds fluctuates widely with concentration peaks of nitrogen compounds in excess of about 50 ppm-wt, then it is preferred that at least two adsorbent beds operating with at least one adsorbent bed treating the hydrocarbon phase stream 18, while the other bed is regenerated, be employed to provide adsorption of nitrogen compounds in a continuous manner. In the alternate operation, the concentration of nitrogen compounds in the adsorbent effluent is monitored and when the concentration of nitrogen compounds exceeds about 0.1 ppm-wt acetonitrile, the hydrocarbon phase is passed to the second adsorbent bed which has been previously regenerated and the first adsorbent bed is regenerated in the conventional manner.

The invention will be further clarified by a consideration of the following examples, which are intended to be purely exemplary of the use of the invention.

EXAMPLES

Example I

A series of adsorbents were evaluated for their relative selectivity to adsorb acetonitrile from a solution of acetonitrile and benzene. In a commercial plant, the benzene will range from dry benzene, having essentially no water and wet benzene at saturation conditions of about 500 ppm-wt water. Acetonitrile was added to the benzene solutions at levels of about 0.08 wt-% and 0.45 wt-% in benzene. Water saturated benzene was prepared by adding water to benzene, shaking the benzene/water mixture and allowing the mixture to stand over night. A measured amount of water saturated benzene mixture was withdrawn from the hydrocarbon phase and admixed with an amount of acetonitrile. Shake tests were conducted by activating the adsorbents at 200° C. and allowing them to return to room temperature in a desiccator in a conventional manner prior to testing. A one gram sample of each adsorbent was placed into a 22 cc sealable septum vial with a measured amount (about 10 grams) of benzene solution. The samples were shaken on a rocker apparatus to keep the solution well-mixed and in contact with the adsorbent for a period of from 1 to 2 hours. The liquid phase was sampled and analyzed by gas chromatography with a flame ionization detector. The adsorbed phase was determined by difference. The results of a 1 hour and a 2 hour adsorption tests are shown in Table 1 for a 4A molecular sieve adsorbent with both a wet benzene solution and a dry benzene solution containing about 0.08 and about 0.45 wt % acetonitrile.

TABLE 1

ACN ADSORPTION ON 4A SIEVE WITH BENZENE PRESENT

| FEED | 1 HOUR % ACN REMOVAL | 2 HOUR % ACN REMOVAL |
|---|---|---|
| 0.08% ACN/BENZENE, DRY | >99 | >99 |
| 0.08% ACN/BENZENE, WET | >99 | >99 |
| 0.42% ACN/BENZENE, DRY | 85 | 94 |
| 0.46% ACN/BENZENE, WET | 83 | 86 |

The results of the adsorption with 4A molecular sieve confirm the ability of the adsorbent to remove acetonitrile with a removal efficiency of greater than about 80%. A removal rate of ACN greater than 80% should provide adequate protection for the alkylation catalyst when the benzene feed is partially or fully saturated with water.

Example II

A series of shake tests, as described in Example I, were prepared using hydrophobic adsorbents to avoid the adsorption of water. In this way, the adsorption of the nitrogen compound impurity would not be limited by the adsorption of water, thus providing a more stable process with less frequent regeneration. Silicate and F-silicalite are hydrophobic, but both adsorb benzene. Example II evaluates the capability of silicate and F-silicate to adsorb ACN in the presence of benzene. The procedure of Example I was repeated with fresh silicalite and F-silicalite, and silicalite and F-silicalite which had been saturated in 100% liquid benzene over night to saturate the benzene adsorption capacity of the adsorbent. The ACN removal rates from a feed containing 1% ACN, 10% benzene and the balance o-xylene over a 1 gram sample of each adsorbent is summarized in Table 2.

TABLE 2

ACN ADSORPTION ON SILICATE

| ADSORBENT | 1 HOUR % ACN REMOVAL | 2 HOUR % ACN REMOVAL |
|---|---|---|
| SILICALITE | 30.2 | 47.7 |
| F-SILICALITE | 27.1 | 26.1 |
| SILICALITE/BENZENE | 34.0 | 37.2 |
| F-SILICALITE/BENZENE | 27.6 | 31.0 |

The results of the ACN removal rates of Example II indicate that the ACN removal over silicalite and F-Silicalite was not limited by the presence of benzene and, surprisingly, that ACN successfully competed with benzene for adsorption on these silicalite materials.

Example III

A feedstream comprising benzene, water and acetonitrile (ACN) is passed to a drying column of the present invention as shown in the FIGURE. The feedstream contains about 10 ppm-wt ACN and is water saturated with about 500 ppm-wt water. The drying column contains about 11 theoretical trays and the feedstream is introduced at a feed point near the top of the column to provide an overhead stream and a bottoms product. The overhead stream is condensed and separated into a hydrocarbon phase and an aqueous phase. The hydrocarbon phase or reflux stream is returned to the drying column at a point below the above feed point following treatment in an adsorption zone containing an adsorbent selective for the adsorption of ACN from the benzene such as silicalite or F-silicalite. The bottoms product from the drying column contains about 0.1 ppm-wt ACN. The distillate, or aqueous stream is withdrawn as waste water. The overall column operates at a reflux ratio which is the ratio of the reflux to the distillate of greater than 100.

Example IV

In the operation of the process of the present invention during a regeneration mode, the column operates as described in Example III, except that the adsorption zone is by-passed and all of the reflux is returned directly to the drying column. The aqueous stream continues to be withdrawn. During this regeneration mode operation, the concentration of the ACN impurity builds up throughout the drying column. Although the ACN is passed overhead with the water, its solubility in water is minimal and, as a result, the concentration of ACN in the bottoms product increases toward the concentration of ACN in the benzene feedstream with a time constant which represents the time required for the concentration of ACN in the bottoms product to reach 63% of its equilibrium value which is equal to the concentration in the benzene feedstream. Surprisingly, it was discovered that the time constant for the drying column of Example III is about 20 hours for this configuration. The 20 hour time constant in the drying column permits the invention to be operated with a single adsorbent bed while providing sufficient time to regenerate the adsorbent bed during the by-passing regeneration mode while the hydrocarbon phase stream around adsorbent bed. The adsorbent bed is regenerated by conventional means in less than about 5 to 6 hours. Following desorption with hot desorbent, the bed is cooled to adsorption conditions by passing a portion of the bottoms product through the adsorption bed. Upon switching the adsorption bed to the adsorption mode, the contents of the bed are returned to the drying column.

Example V

To further illustrate the advantages of the present invention for feedstreams subject to a concentration spike of impurity, these scenarios are compared for managing a spike equivalent to 100 times the ACN content of Example III for a period of one hour. The three scenarios are as follows:

A two adsorption beds are provided to treat the entire wet feedstream at the concentration of the spike B a tank equivalent to 20 hours of hold-up time precedes an adsorption bed C the process of the present invention with two adsorption beds and a drying column In order to manage a concentration spike of 100 times normal concentration of impurity, the relative size of the adsorption zone is shown in Table 1A by a relative bed size factor (BSF).

TABLE 1A

RELATIVE ADSORPTION BED SIZE REQUIREMENT

| SCENARIO | RELATIVE BED SIZE |
|---|---|
| A | 10,000 |
| B | 500 |
| C | 100 |

In scenario A, the adsorption beds deactivate at a rate 100 times faster than normal and the impurity breakthrough occurs at the feed concentration, contaminating the catalyst and resulting in the premature failure of the alkylation catalyst or requiring a bed with a 10,000 BSF to prevent such a breakthrough of impurity. In scenario B, the hold-up tank provides a 20:1 dilution, increasing the concentration of the impurity to about five times the normal level. Thus, breakthrough occurs 5 times faster than normal, requiring sufficient adsorbent to overcome the spike and prevent breakthrough. In scenario B an adsorbent bed with a 500 BSF is required to prevent breakthrough. In scenario C, a scheme based on the present invention wherein the breakthrough effluent is returned to the drying column with a 20 hour time constant—as described in EXAMPLE IV—requires an adsorption zone with a BSF of about 100.

We claim:

1. A process for the removal of nitrogen compounds from an aromatic hydrocarbon stream comprising nitrogen compounds and mixtures thereof with water, said process comprising passing said stream to an adsorption zone containing an adsorbent selective for the adsorption of said nitrogen compounds, said adsorbent comprising a non-acidic molecular sieve having a silica to alumina ratio in excess of about 100 and an average pore size less than about 5.5 Angstroms and withdrawing a treated effluent being essentially free of said nitrogen compounds.

2. The process of claim 1 wherein said nitrogen compounds are selected from the group consisting of acetonitrile, propionitrile, acrylonitrile and mixtures thereof.

3. The process of claim 1 wherein said aromatic hydrocarbon stream comprises benzene.

4. The process of claim 1 wherein the water comprises from about 10 ppm wt to about 2 wt %.

5. The process of claim 1 wherein said treated effluent comprises less than 10 ppm wt of said nitrogen compounds.

6. The process of claim 1 wherein said treated effluent comprises less than 1 ppm wt of said nitrogen compounds.

7. The process of claim 1 wherein said non-acidic molecular sieve is selected from the group consisting of silicalite, F-silicalite, ZSM-5, ferrierite, and mixtures thereof.

8. The process of claim 7 wherein said non-acidic molecular sieve is bonded with a binder comprising silica.

9. The process of claim 8 wherein said non-acidic molecular sieve comprises silicalite or F-silicalite.

10. The process of claim 1 wherein said aromatic hydrocarbon stream comprises from about 10 to about 100 vol % aromatic hydrocarbons.

11. The process of claim 1 wherein said effluent stream is passed to a reaction zone containing an acidic catalyst.

12. The process of claim 11 wherein said reaction zone comprises an alkylation reaction.

13. A process for the removal of a nitrogen compound from a mixture comprising said nitrogen compound, water, and an aromatic hydrocarbon component said process comprising:

a) passing said mixture to a fractionation zone to provide an overhead stream comprising said nitrogen compound, water, and said aromatic hydrocarbon component and a bottoms product stream being essentially free of said nitrogen compound;

b) cooling and condensing said overhead stream to produce a hydrocarbon phase stream comprising said nitrogen compound, water, and said hydrocarbon component and an aqueous phase stream comprising said nitrogen compound and withdrawing said aqueous phase stream;

c) passing said hydrocarbon phase stream to an adsorption zone containing an adsorbent selective for the adsorption of said nitrogen compound to provide a treated effluent stream essentially free of said nitrogen compounds and retuning said treated effluent to said fractionation zone;

d) terminating the passing of said hydrocarbon phase stream to said adsorption zone prior to the breakthrough of said nitrogen compound, returning at least a portion of said hydrocarbon phase stream to said fractionation zone, and regenerating said adsorption zone to provide a regenerated adsorption zone; and e) terminating the return of said hydrocarbon phase of step (d) and resuming the passing of said hydrocarbon phase stream to said regenerated adsorption zone to provide a continuous process.

14. The process of claim 13 wherein said mixture comprises less than 100 ppm-wt of said nitrogen compound.

15. The process of claim 13 wherein said bottoms product comprises greater than about 99 percent of said hydrocarbon component.

16. The process of claim 13 wherein said mixture comprises from about 0.001 to about 20 mol-% nitrogen compound.

17. The process of claim 13 in said mixture comprises less than 600 ppm-wt water.

18. The process of claim 13 wherein said aromatic hydrocarbon component is selected from the group of benzene, toluene, xylenes, naphthalene antracene, phenanthrene substituted mono- and poly- derivatives thereof, and mixtures thereof.

19. The process of claim 13 wherein said nitrogen compound is selected from the group consisting of acetonitrile, propionitrile, acrylonitrile, and mixtures thereof.

20. The process of claim 19 wherein said bottoms product being essentially free of said nitrogen compound comprises from about 0.1 ppm-wt to about 10 ppm-wt of said nitrogen compound.

21. The process of claim 13 further comprising cooling said regenerated adsorption zone to adsorption conditions with at least a portion of said bottoms product stream to provide a heated bottoms product stream and passing said heated bottoms product stream to an alkylation reaction zone.

22. The process of claim 13 wherein said adsorbent comprises a non-acidic molecular sieve having a silica to alumina ratio in excess of about 100 and an average pore size of less than about 5.5 Angstroms.

23. The process of claim 22 wherein said adsorbent is selected from the group consisting of silicalite, F-silicalite, ZSM-5, ferrierite, and mixtures thereof.

24. The process of claim 13 wherein said adsorbent is a molecular sieve having an average pore size of less than about 5.5 Angstroms and is selected from the group consisting of pore-closed zeolite 4A, zeolite 4A, silicalite, F-silicalite, ZSM-5, and mixtures thereof.

25. The process of claim 9 wherein the non-acidic molecular sieve is present in a silica matrix in amounts ranging from about 75 wt-% to about 98 wt-%.

* * * * *